United States Patent [19]

Mesek et al.

[11] 4,235,237

[45] Nov. 25, 1980

[54] ABSORBENT OPEN NETWORK STRUCTURE

[75] Inventors: Frederick K. Mesek, Tinley Park; George A. M. Butterworth, Western Springs; Talivaldis Cepuritis, Kenilworth, all of Ill.

[73] Assignee: Johnson & Johnson, New Brunswick, N.J.

[21] Appl. No.: 904,056

[22] Filed: May 8, 1978

[51] Int. Cl.³ .............................................. A61F 13/16
[52] U.S. Cl. ................................... 128/284; 128/287; 128/290 R
[58] Field of Search ............... 128/284, 287, 290, 296; 260/17.4 GC; 526/55; 428/286, 264

[56] References Cited

U.S. PATENT DOCUMENTS

| 3,371,667 | 3/1968 | Morse | 128/290 R |
|---|---|---|---|
| 3,670,731 | 6/1972 | Harmon | 128/284 |
| 3,686,024 | 8/1972 | Nankee et al. | 128/284 |
| 3,888,256 | 6/1975 | Studinger | 128/284 |
| 3,890,974 | 6/1975 | Kozak | 128/287 |
| 3,901,236 | 8/1975 | Assarsson et al. | 128/284 |
| 3,903,889 | 9/1975 | Torr | 128/287 |
| 4,051,086 | 9/1977 | Reid | 128/284 |
| 4,061,846 | 12/1977 | Gross et al. | 128/284 |
| 4,076,663 | 2/1978 | Masuda et al. | 128/284 |
| 4,102,340 | 7/1978 | Mesek et al. | 128/287 |
| 4,115,332 | 9/1978 | Young et al. | 128/284 |

Primary Examiner—C. Fred Rosenbaum
Attorney, Agent, or Firm—Martha A. Michales

[57] ABSTRACT

An absorbent open network has water-insoluble but water-swellable particles spaced from one another but integral with the network to provide an absorbent structure which is useful as an element in a disposable, body fluid-absorbing article, such as a disposable diaper, sanitary napkin, or the like. Also disclosed are methods for making the absorbent open network structure, and disposable diapers incorporating such absorbent structures.

1 Claim, 6 Drawing Figures

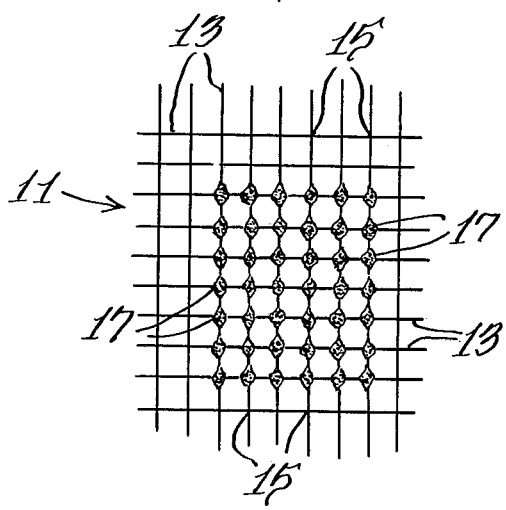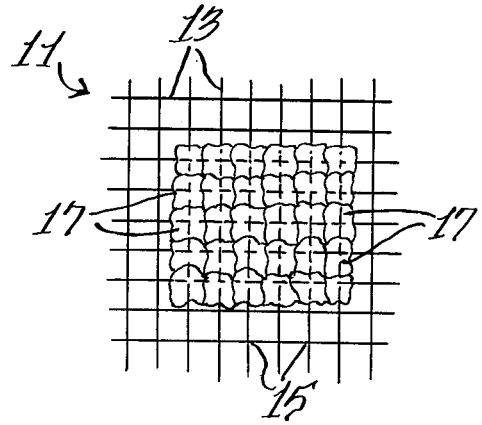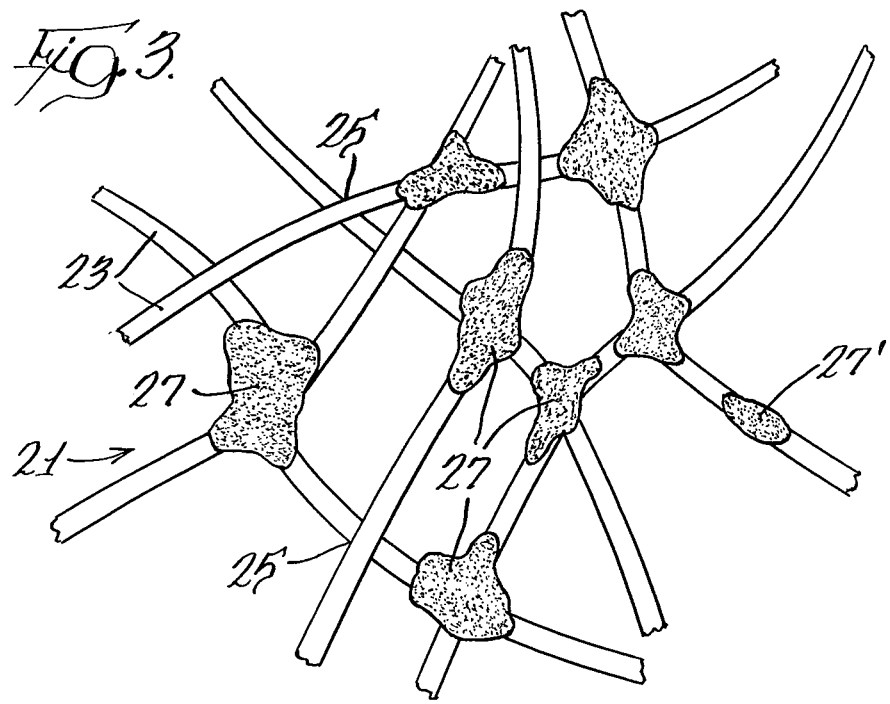

ABSORBENT OPEN NETWORK STRUCTURE

BACKGROUND OF THE INVENTION

This invention relates to disposable absorbent articles such as disposable diapers, sanitary napkins and the like.

Disposable diapers provide substantial advantages in convenience over diapers intended to be laundered and reused, particularly when the diapers are used away from home. In recent years, many different disposable diapers have been proposed and some have been successful in the marketplace. However, even the successful diapers are not altogether satisfactory in such functions as keeping moisture away from an infant's skin and in absorbing relatively large amounts of urine. In spite of this, these diapers have been a commercial success because consumers have been willing to accept their inadequate performance as part of the price for convenience.

In one form of a prior disposable diaper, creped cellulose wadding is used as the absorbent material, covered with a permeable paper-like facing material on the side to be brought into contact with the infant's skin and covered with an impervious plastic sheet on the outside. In such a diaper, the wadding becomes more or less uniformly saturated with urine as the infant voids, and thus a substantial amount of moisture is only a paper's thickness away from the infant's skin. In use, the weight of the infant presses the paper-like facing layer against the saturated wadding so that substantial amounts of moisture are expressed from the diaper and pass through the facing and into contact with the infant's skin.

In attempting to increase the ability of the disposable absorbent diaper to keep moisture away from the portion of the diaper which comes into contact with an infant's skin, it has been proposed to loosely distribute water-insoluble but water-absorbent particulate material into the absorbent region of a disposable diaper. Such particulate matter is disclosed in U.S. Pat. No. 3,669,103 to Harper, et al., U.S. Pat. No. 3,670,731 to Harmon, and U.S. Pat. No. 3,783,872 to King. However, such particulate matter tends to swell and form a gelatinous layer which, while absorbent, tends to block the liquid passage therethrough. As a result, the full absorptive capacity of the article is not utilized because liquid to be absorbed cannot reach the absorbent material. In addition, the loosely distributed particulate matter tends to migrate to the bottom of the absorbent region of the diaper, further reducing its efficiency for its intended purpose.

An interesting method of anchoring water-insoluble but water-swellable particles in a fibrous material, such as in the absorbent layer of a disposable diaper, has been proposed in U.S. Pat. No. 3,901,236 to Assarssan, et al., which concerns a method for producing hydrogel particles which have a fibrous coating. The patentee maintains that the fibrous coating on the hydrogel particles will interlock with the fibers in a fibrous material in which the hydrogel particles are deposited, such that the hydrogel particles will be prevented from migrating during handling of the fibrous material.

U.S. Pat. No. 3,888,256 to Studinger, presents another method of utilizing the absorptive capacity of the water-absorbent particulate material. It provides for a diaper in which a particulate swelling substance is arranged exclusively or additionally in one of the layers lying near that surface of the diaper which is adjacent the baby's skin when the diaper is worn, i.e., the diaper facing sheet. The particles are distributed throughout this layer in an arrangement such that the spacing between particles is no greater than half of the particle diameter increase which occurs upon swelling of the particles. This arrangement allows the initial flow of urine to pass through the top particulate-containing layer into the absorbent layer. While this is occurring, the absorbent particles are absorbing liquid at such a rate that by the time the liquid has passed to the absorbent layer, the particles will have swelled to form a barrier layer, thus preventing the liquid from passing back through the diaper facing and in contact with the skin when the wet diaper is compressed. Ideally, this barrier layer should prevent the back flow of liquid even when substantial pressure is applied to the diaper, such as when an infant sits down on the diaper.

The top layer of U.S. Pat. No. 3,888,256 is formed by adhering the particles to a surface of a sheet-form liquid-pervious carrier in a two-step process which consists of treating the liquid-pervious support sheet with an adhesive, and then sprinkling the layer of adhesive with the particles. Inasmuch as a portion of the particle surface is necessarily in contact with the adhesive, the total surface available for liquid absorption is materially reduced.

U.S. Pat. No. 3,890,974 to Kozak discloses a diaper containing a slitted hydrogel film which functions in the same manner as the facing of the diaper shown in the aforementioned U.S. Pat. No. 3,888,256. The slitted hydrogel film is disclosed as being a hydrophilic, substantially water-insoluble film disposed between the top sheet of a diaper and the backing sheet. The film contains a plurality of short slits, i.e., 1/16 to ⅜ inch in length, so that aqueous liquid contacting the film causes the film to swell and to thereby open the slits to permit passage of liquid therethrough. This film initially allows the passage of liquid through the slits, and by carefully controlling the length of the slits, prevents the liquid from passing back through the slits in the opposite direction. It is disclosed in this patent that the length of the slits must be carefully controlled to accomplish this result. An obvious disadvantage of this method is that a high degree of quality control is essential to the accomplishment of the purpose set forth in the patent.

In Weaver, et al., "Highly Absorbent Starch-Based Polymer", presented to the International Nonwovens and Disposable Association in Washington, D.C., on March 5-6, 1974, it is reported that graft copolymers of starch and polyacrylonitrile may be hydrolyzed by a base to convert the nitrile functionality thereof to a mixture of carboxamide forms and alkali metal carboxylate forms. According to Weaver, et al., while the alkali metal carboxylate form of the graft copolymer had only limited solubility in water, dispersions of the carboxylate form thereof dry to continuous films on various substrates. These dried films do not redissolve on addition of water, but instead swell tremendously, imbibing several hundred times their weight in water. Weaver, et al., further reports that particles of this type of absorbent material have been incorporated into absorbent batt layers of diapers in powder form.

SUMMARY OF THE INVENTION

This invention provides an improved method of anchoring, in a spaced relationship to one another, particulate water-insoluble but water-swellable materials intended for incorporation into absorbent articles, such as diapers, as well as absorbent articles produced according to this method.

The method of this invention comprises providing a fluid substance constituted of potentially water-insoluble but water-swellable absorbent particles distributed in a liquid carrier, and contacting an open network with the fluid substance so as to deposit beads of the fluid substance on the open network structure, preferably at junctions of the network elements. Next, the liquid carrier is removed (e.g., by vaporization) from the deposited beads so that a solid absorbent residue consisting essentially of water-insoluble but water-swellable particles remains anchored to the open network and integral therewith.

In preferred embodiments of this invention, the open network may be a three-dimensional structure formed by a plurality of fibers in random point contact with one another or a slab of an open cell foam. A woven scrim, such as gauze, having a plurality of warp and weft intersections, also provides a suitable open network. When such open networks are contacted with the fluid substance containing the absorbent particles, such as by dipping or spraying, beads of the fluid substance are deposited primarily on a plurality of the intersections of the structure and also to a lesser extent on free fiber lengths between intersections. Subsequent vaporizing of the liquid component of the fluid substance results in retention of the water-insoluble but water-swellable absorbent particles integral with the structure primarily at intersections thereof and to a lesser extent randomly along free fiber lengths, thus providing an absorbent open network structure with spaced-apart water-swellable particles that are readily accessible.

The absorbent article of this invention may be incorporated into the structure of a disposable diaper to create a disposable diaper which has greatly improved absorbency as well as effectiveness in keeping moisture away from an infant's skin. A diaper embodying this invention usually includes a moisture impermeable backing sheet which is substantially co-extensive with a facing sheet, and an absorbent batt layer situated between the backing sheet and facing sheet. The absorbent-bearing open network can be situated between the facing sheet and the absorbent batt layer, sandwiched between a pair of absorbent layers, or can be situated between the absorbent batt layer and the backing sheet.

When a baby voids into a diaper constructed so that the absorbent-bearing open network is positioned between the facing sheet and an absorbent batt layer, the urine will initially pass through the facing layer and the open network structure into the absorbent batt layer. As this is occurring, the spatially distributed water-swellable particles in the open network begin to swell as they begin to absorb the excreted body fluid. When the particles are fully swollen, they form a barrier which prevents the excreted body fluid from flowing back from the absorbent batt layer to the infant's skin even when the absorbent batt layer is saturated and is subjected to pressure which would otherwise force the body fluids out of the batt layer and back through the facing sheet to the infant's skin.

BRIEF DESCRIPTION OF THE DRAWINGS

FIG. 1 is a fragmentary plan view of a substantially planar absorbent open network having water-swellable particles integral therewith;

FIG. 2 is a fragmentary plan view of the open network shown in FIG. 1 with the water-swellable particles in a swollen condition;

FIG. 3 is an enlarged fragmentary perspective view of a three-dimensional open network having unswollen water-insoluble but water-swellable fibers integral therewith;

DETAILED DESCRIPTION OF THE DRAWINGS

Figure 4:
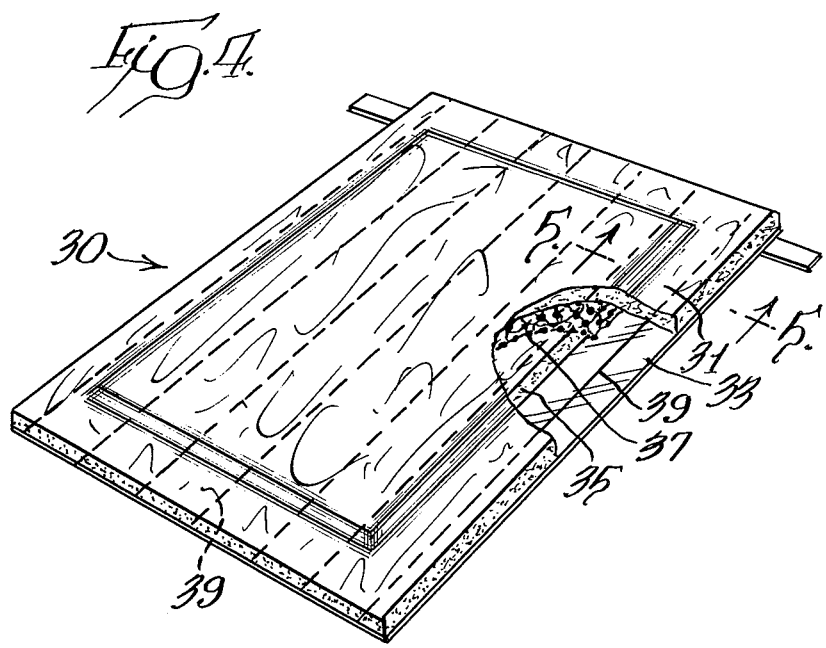
FIG. 4 is a perspective view of an open unfolded diaper in accordance with an embodiment of the invention, parts of the diaper being broken away to show internal construction.

Referring to FIG. 1, the substantially planar open network 11 comprises a plurality of fibers 13 crossing one another to define junctions or intersections 15 wherein the fibers are in at least point contact. Water-insoluble but water-swellable particles 17 in the unswelled condition substantially surround and are integral with the fibers 13. FIG. 2 shows the open network structure 11 with the particles 17 in the swollen condition, i.e., after body fluid absorption. The particles are distributed in the network in such a manner that the swelled particles form a sheet of gel which is substantially impermeable to the flow of liquids.

FIG. 3 shows a three-dimensional open network structure 21 having fibers 23 which cross one another to define intersections or junctions 25. Unswollen water-insoluble but water-swellable particles 27 substantially surround and are integral with the fibers 23. The particles 27 are disposed mainly at the intersections 25, although some particles may be disposed on a non-intersecting portion of a fiber, such as particle 27'.

The method of making the absorbent open network structure 11 of this invention is carried out by first distributing potentially water-insoluble but water-swellable absorbent particles as a dispersion, suspension, or solution in a liquid carrier to produce a fluid substance. Next, the open network is contacted with the produced fluid substance by immersion, spraying, etc., so as to deposit beads of the fluid substance on the open network. Thereafter, the liquid carrier is vaporized, such as by exposure to air at room or elevated temperatures, from the beads of the fluid substance to leave a residue comprising the water-insoluble but water-swellable material on the open network structure and integral therewith.

Suitable illustrative open network structures include fibrous batts, filament layers, sponges, open-cell flexible synthetic foam, woven scrims having a plurality of warp and weft intersections, reticulated monofilament networks, and the like. Preferably, the open network structure will have a plurality of fibers or filaments defining intersections. Such intersections may be defined by a plurality of fibers or filament, in random point contact with one another, by a plurality of warp and weft intersections in a woven scrim such as gauze, by junctions of a plurality of monofilaments, or the like.

Suitable liquid carriers are those that wet the open network and include water and organic solvents which dry quickly when exposed to air and which do not leave a solvent residue which may be irritating to an infant's skin. If necessary, wetting of the open network can be enhanced by adding a surfactant. Suitably, the potentially water-insoluble but water-swellable particles are distributed in the liquid carrier in an amount such that a random bead or droplet taken from the fluid substance will contain, on the average, at least one water-insoluble but water-swellable particle. This can be accomplished by forming a suspension or solution in which the water-insoluble but water-swellable particles constitute from about 1 to about 10 percent by weight of the total solution. Preferably, the water-swellable particles are dispersed in the liquid carrier in an amount of from about 2 to 8 percent by weight. When an open network fibrous structure having intersecting fibers is contacted and subsequently removed from contact with the fluid substance, beads of the fluid substance will remain on the fibers, and mainly at intersections of the fibers. After the liquid substance is vaporized from the beads of fluid substance on the open network structure, the water-swellable particles such as particles 17 and 27 will remain deposited on and integral with the fibers at the intersection. By the phrase "integral with the fibers," it is meant that the particles are retained by the fibers or filaments forming the open network as the liquid carrier is vaporized. For example, the particles may generally conform to the shape of the fibers during the vaporizing process and may partially or fully envelop the fibers. Similarly, a particle contained in a bead of fluid substance disposed in an intersection of two or more fibers may conform to the surface of both intersecting fibers at the intersections and partially envelop each fiber. This condition is illustrated in FIG. 3 which is a three-dimensional enlarged view of an open network structure 21 having fibers 23 in random point contact. Most of the water-insoluble but water-swellable particles 27 are integral with the structure at the points of contact or intersections 25 of the fibers, although a few particles 27' are disposed on non-intersecting portions of the fibers.

Suitable water-insoluble but water-swellable particles 15 contemplated herein include particulate absorbent material having at least about 25 percent of their molecular structure composed of hydrophilic groups and capable of retaining water in an amount which is at least ten times the weight of the absorbent material in dry form and preferably about fifteen to seventy times the weight, or more. These particulate materials have a particle size of about 1 to $10^3$ microns. A more complete description of these particles is set forth herein below.

Illustrative of the water-insoluble but water-swellable particles used in this invention are the so-called hydrocolloid absorbent materials which are water-insoluble, for example, the cross-linked polyacrylamides, cross-linked sulfonated polystyrenes, mixtures of the foregoing, and the like. Preferred are the hydrolyzed polyacrylamides having the general formula

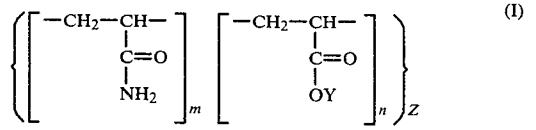
(I)

wherein Y is a hydrogen, ammonium, or an alkali metal ion, m is an integer having a value of 1 to 100, n is an integer having a value of 0 to 100, the sum of m plus n is 100, and Z in an integer having a value of 1 to 30, where Z times 100 is equal to the number of mer units between crosslinks. These materials are known in the art and are described in U.S. Pat. No. 3,229,769 and U.S. Pat. No. 3,670,731.

The aforesaid polyacrylamide-type absorbent materials can be prepared by cross-linking a linear polyacrylamide with a non-conjugated divinyl compound such as methylene-bis-acrylamide. Alternatively, an acrylamide can be copolymerized. The polymerization techniques for these materials are known in the art and include the use of peroxide catalysts, photopolymerization with a riboflavin activator, and similar methods.

The cross-linking compound can be present in an amount of about 500 to about 5,000 parts per million parts of the polymerizate. Other illustrative non-conjugated divinyl cross-linking compounds are 1,4-divinyl benzene, N,N-diallylacrylamide, diallylamine, diallylmethacrylamide, 2,5-dimethyl-1,7-octadiene, p,p'-diisopropenylbezene, 2,8-dimethyl-1,8-nonadiene, diethylene glycol divinyl ether, and the like.

Particularly preferred particulate polyacrylamides for the present purposes are those in Formula I that are hydrolyzed and wherein Y is sodium or potassium, n has a value of about 10 to about 70 and Z has a value of about 2 to 20. Most preferred are the hydrolyzed polyacrylamides wherein Y is a sodium, n has a value of about 20 to about 40, and Z has a value of about 4 to about 15.

The cross-linked polystyrene sulfonates suitable for the present purposes can be represented by the formula

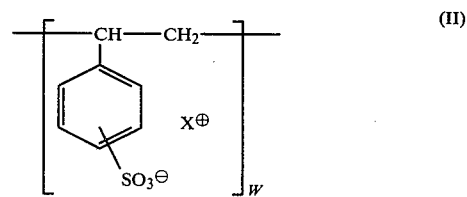
(II)

wherein X is a hydrogen, ammonium, or alkali metal ion and W is an integer having a value of about 100 to 3,000 and defines the number of mer units between crosslinks. The foregoing crosslinked polystyrene sulfonates are well known in the art and are described in U.S. Pat. No. 3,670,731. The polystyrene sulfonates of Formula II can be prepared by copolymerizing styrene with a non-conjugated divinyl compound such as divinyl benzene in the presence of a polymerization catalyst such as benzoyl peroxide. To produce the desired particulate form of this absorbent material, a suspension stabilizer such as gelatin or polyvinyl alcohol can be added to the polymerization mixture. The produced polymer is then sulfonated by heating in the presence of concentrated sulfuric acid at a temperature of about 100° C.

Another grouping of suitable particulate absorbent materials comprises cross-linked poly (alkylene oxides) and the alkyl-substituted phenyl ethers thereof. The cross-linked poly (alkylene oxides) contain at least one of the following units:

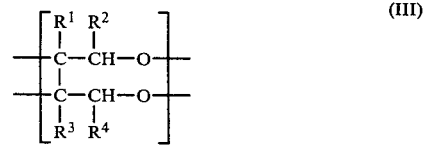
(III)

-continued
or

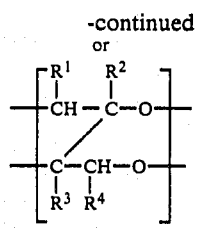

wherein $R^1$, $R^2$, $R^3$ and $R^4$ can be hydrogen, lower alkyl, lower alkenyl, and aryl; preferably methyl, vinyl, and phenyl, respectively.

The cross-linked polymers of the type shown in Formulas III and IV are described in U.S. Pat. No. 3,783,872 and can be formed by preparing a substantially homogeneous aqueous solution of a water-soluble compound having the formula

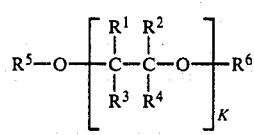

wherein $R^1$–$R^4$ are the same as in Formulas III and IV, above, $R^5$ and $R^6$ are hydrogen, alkyl or alkaryl, and K is an integer having a value greater than 1, and subjecting the prepared solution to ionizing radiation for a time period sufficient to insolubilize the dissolved reactants. The preferred compounds within the purview of Formula V are ethylene oxide polymers having a reduced viscosity of at least about 0.5 and up to about 75, or an aqueous viscosity of about 225 centipoises to about 12,000 centipoises, measured as a 1 weight, percent solution at 25° C. Particularly suitable are the ethylene oxide homopolymers and the ethylene oxide copolymers, terpolymers, and the like, containing up to about 50 percent by weight at least one other lower olefin oxide such as propylene oxide, butylene oxide, styrene oxide, and the like.

Still other suitable particulate polymeric absorbent materials are polyelectrolytes such as the water-insoluble, cross-linked copolymers of maleic anhydride and ethylene, as well as the hydrophilic maleic anhydride copolymers with vinyl methyl ether, divinyl ether, vinyl acetate, isobutylene, styrene, and similar unsaturated monomers. Generally, the foregoing polymeric polyelectrolytes are prepared by reacting ethylene or other unsaturated monomer or mixtures thereof, as previously described, with the acid anhydride in the presence of a peroxide catalyst in an aliphatic or aromatic hydrocarbon solvent for the monomers but nonsolvent for the interpolymer formed. Suitable solvents include benzene, toluene, xylene, chlorinated benzene and the like. While benzoyl peroxide is usually the preferred catalyst, other peroxides such as acetyle peroxide butyryl peroxide, ditertiary butyl peroxide, lauroyl peroxide and the like, or any of the numerous azo catalysts, are satisfactory since they are soluble in organic solvents. The copolymer preferably contains substantially equimolar quantities of the olefin residue and the anhydride residue. Generally, it will have a degree of polymerization of 8 to 10,000 preferably about 100 to 5,000, and a molecular weight of about 1,000 to 1,000,000, preferably about 10,000 to 500,000. The properties of the polymer, such as molecular weight, for example, are regulated by proper choice of the catalyst and control of one or more of the variables such as ratio of reactants, temperature, and catalyst concentration or the addition of regulating chain transfer agents, such as diisopropyl benzene, propionic acid, alkyl aldehydes, or the like. The product is obtained in solid form and is recovered by filtration, centrifugation, or the like. Removal of any residual or adherent solvent can be effected by evaporation using moderate heating. Numerous of these polymers are commercially available. Particularly useful copolymers are those derived from ethylene and maleic anhydride in approximately equimolar proportions. The product is commercially available in various molecular weights, e.g., having molecular weights of about 2,000–3,000, 20,000–30,000, and 60,000–80,000 any of which may be used for preparation of products employed in the present invention, since insolubilization by crosslinking leads to an indefinite molecular weight product.

The maleic anhydride copolymers thus obtained have repeating anhydride linkages in the moleculare, which are readily hydrolyzed by water to yield the acid form of the copolymer, rate of hydrolysis being proportional to temperature.

Also, some of the aforementioned absorbent materials that are anchored on the open network structures in accordance with the present invention are initially water-soluble at a certain water temperature but are rendered substantially water-insoluble once the water is removed by vaporization, or by irradiation while in an aqueous solution in a manner known in the art prior to the vaporization of the water carrier.

Another preferred type of particulate absorbent material suitable for the present purposes is a graft copolymer of a water-insoluble polysaccharide such as starch or cellulose having hydrophilic chains of carboxylcarboxylate-, and/or carbamide-bearing moieties.

Water-insoluble starch or a wide variety of cellulosic fibers can be utilized as starting materials for producing graft copolymers of this general type. Typical such cellulosic fibers are: cotton, cotton linters, wood pulp, bagasse pulp, jute, rayon, and the like. The polysaccharide chains are then modified by grafting thereon a hydrophilic chain of the general formula

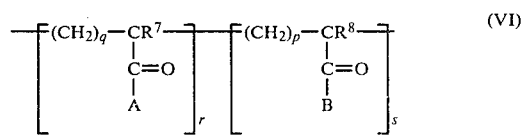

A and B are selected from the group consisting of —$OR^9$, —0 (alkali metal), —$OHNH_3$, —$NH_2$, wherein $R^7$, $R^8$, and $R^9$ are selected from the group consisting of hydrogen and alkyl having 1 to 4 carbon atoms, wherein r is an integer having a value of 0 to about 5000, s is an integer having a value of 0 to about 5000, r plus s is at least 500, p is an integer having a value of zero or 1, and q is an integer having a value of 1 to 4.

Preferred hydrophilic chains are hydrolyzed polyacrylonitrile chains and copolymers of polyacrylamide and sodium polyacrylate. In another preferred embodiment both ionizable polymeric moieties and non-ionizable polymeric moieties can be grafted on the same polysaccharide backbone.

While the detailed mechanism by which the grafting of the hydrophilic chain or chains onto a starch or a cellulosic backbone is not fully known, it is believed that grafting takes place through a free radical mechanism whereby the free radical is situated on the backbone which serves as a reducing agent, and the hydrophilic chain is attached to the starch or cellulosic reducing agent through a carbon linkage. The produced graft copolymer using a cellulosic backbone is of the type

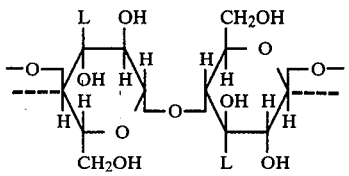

wherein L represents the hydrophilic chain of Formula VI above. The graft copolymer using a starch backbone is substantially similar to that represented by Formula VI except that a starch backbone is present in lieu of a cellulosic backbone.

The foregoing hydrophilic chains are polymers of an olefinically unsaturated carboxylic acid or a derivative thereof with itself or in approximately equimolar amounts with at least one other monomer copolymerizable therewith. The resulting polycarboxylic acid-type polymers can be of the nonvicinal type including those containing monomer units such as acrylic acid, acrylic anhydride, methacrylic acid, crotonic acid or their respective derivatives, including partial salts, amides and esters thereof, or of the vicinal type including maleic acid, itaconic acid, citraconic acid, alpha-dimethyl maleic acid, alpha-butyl maleic acid, fumaric acid, aconitic acid, as well as partial salts, amides and esters thereof. Anhydrides of any of the aforesaid acids can also be employed.

Comonomers which can be used with the above functional monomers include alpha-olefins such as ethylene, propylene, isobutylene, 1-butene, 2-butene.

The initial copolymers of anhydrides with another monomer can be converted to carboxyl-containing copolymers by reaction with water, and carboxylate-containing moieties, such as ammonium or alkali salts thereof, by reaction with aqueous solutions of alkali metal compounds such as sodium hydroxide, potassium hydroxide, and the like or with aqueous ammonia.

The copolymers are formed in a known manner by reacting admixtures of the desired monomers in the presence of a peroxide catalyst in a suitable solvent for the monomers.

The obtained copolymers are conveniently identified in terms of their monomeric constituents. However, the names so applied to the copolymers refer to the molecular structure of the polymer and are not limited to the polymers prepared by the copolymerization of the specific monomers. In many instances, the identical copolymers may be prepared from other monomers and converted to the desired copolymer by a subsequent chemical reaction.

A preferred hydrophilic polymer chain can be prepared by several methods known in the art. Illustrative of such methods are the following:

(1) Polymerize acrylonitrile and hydrolyze with an alkaline solution to form alkali salts of polyacrylic acid.

(2) Polymerize an alkyl acrylate such as methyl acrylate ethyl methacrylate, and the like, and hydrolyze with an alkaline solution to form alkali salts of polyacrylic acid.

(3) Polymerize an alkyl acrylate such as methyl acrylate, ethyl acrylate, butyl acrylate, and the like, and partially hydrolyze so as to produce ionizable and nonionizable polymeric moieties grafted on the polysaccharide backbone.

(4) Polymerize acrylic acid or alkali salts of acrylic acid.

(5) Polymerize methacrylonitrile and hydrolyze with acids to form polymethacrylic acid or hydrolyze with an alkaline solution to form alkali salts of polymethacrylic acid.

(6) Polymerize methacrylic acid or alkali salts of methacrylic acid.

(7) Polymerize acrylamide, optionally followed by hydrolysis.

(8) Polymerize methacrylamide, optionally followed by hydrolysis.

(9) Form copolymers of any of the above monomers or copolymerize with a small amount of non-hydrolyzable monomers.

Methods of graft-copolymerizing olefinically-unsaturated chains onto cellulose and starch are also known in the art. Thus, grafting of the hydrophilic material onto a starch or cellulose backbone can be accomplished simultaneously with the formation of the hydrophilic polymeric material in an aqueous medium, because the peroxide catalyst used to copolymerize the various monomers forms a redox catalyst system in combination with a reducing agent and thus also serves to effect chain transfer onto the starch or cellulose backbone. Suitable reducing agents for this purpose are ceric ion, ferrous ion, cobaltic ion $(NH_4)_2S_2O_8$, cuprous ion, and the like. The desired ions can be supplied in the form of salts such as ceric ammonium nitrate, ferrous ammonium sulfate, and the like. Graft copolymerization of olefinically-unsaturated chains can also be effected by irradiation (ultraviolet-, gamma-, or X-radiation) or by heating in an aqueous medium in the presence of an emulsifier.

Powdered starch or cellulose fibers or pulp can be slurried in water containing a graft copolymerization catalyst system and the monomer or monomers added to the slurry and polymerized in situ at ambient temperatures or above depending on the catalyst employed. In this manner, a portion of the formed hydrophilic polymer may also be physically entrapped into the polysaccharide backbone material during the polymerization process. The preparation of suitable starting materials for practicing the present invention is also illustrated in U.S. Pat. No. 3,256,372.

Hydrophilic chain loading on the polysaccharide backbone can vary from about 10 percent by weight to about 90 percent by weight, and preferably is about 40 to about 80 percent by weight of the graft copolymer.

An extremely water-swellable absorbent material suitable for the present purposes is a starch derivative commercially available from General Mills Chemicals, Inc. under the designation "SG Polymer". This material is prepared by alkaline hydrolysis of starch polyacrylonitrile. The product is polymeric and comprises starch and a synthetic polymer composed of sodium acrylate and acrylamide. Proportions of starch and the synthetic polymer in the product are approximately 2:3, and the proportions of sodium acrylate and acrylamide in the polymer are approximately 3:1.

The term "water-insoluble" means that the product concerned does not dissolve in water or aqueous solutions at ambient temperatures, even though it does have characteristics such as high degree of swelling due to solvation by water, even to the extent of existence in a gel form. Such characteristics are imparted by cross-linking as previously described. The degree of cross-linking, i.e., cross-linking density, relates to the percentage of interchain linkages relative to the total functional units of the polymer.

The novel absorbent open networks prepared in accordance with this invention may be advantageously incorporated in a variety of articles used to absorb body fluids, such as disposable diapers, sanitary napkins, and the like, to produce novel absorbent articles having water-insoluble but water-swellable particles distributed therein in a predetermined arrangement.

When an absorbent open network structure of this invention is intended for use as an upper layer of a diaper, it is highly preferable that the average spacing of the intersections of the fibers be such that when the water-swellable particles integral with the open network structure are fully swollen with water, a gelatinous film will be formed which will be substantially impervious to the passage of water or urine.

Figure 5:
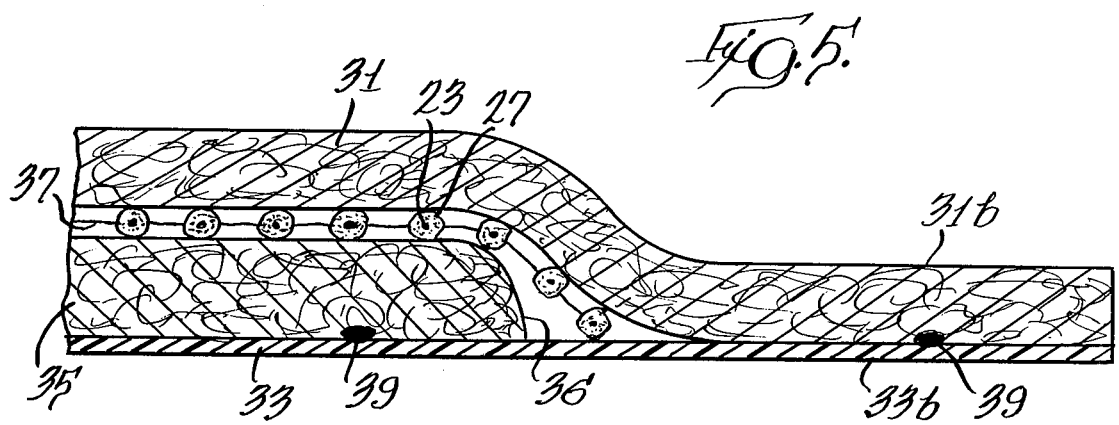
FIG. 5 is a fragmentary cross-sectional elevation of the diaper of FIG. 4 taken along plane 5—5.

FIGS. 4 and 5 show an embodiment of a diaper 30 which incorporates the absorbent open network structure of this invention. The diaper comprises a porous, moisture-permeable facing sheet 31 which forms an inside surface for direction toward an infant, a moisture-impervious backing sheet 33 which forms an outside surface for direction away from the infant, an absorbent pad means 35 situated between backing sheet 33 and facing sheet 31, and an absorbent open network structure 37 of this invention having water-insoluble but water-swellable particles integral therewith situated between the facing sheet 31 and the absorbent pad means 35.

As can be seen from FIG. 4, absorbent pad means 35 is centrally situated on moisture-impervious backing sheet 33 which is of larger dimensions than pad means 35 and is made from a polymeric film which can be smooth or embossed to enhance the drape and feel thereof. The open network 37 is substantially coextensive with and overlies absorbent pad means 35. Preferably, the open network 37 may extend slightly beyond absorbent batt means 35 to form a side barrier against any liquid squeezed out of the side 36 of the batt 35 and back through the facing sheet. Alternatively, the open network 37 may be coextensive with the facing sheet 31 and backing sheet 33.

The batt 35 is secured to the backing sheet 33 by bead lines of adhesive 39 substantially throughout the interface therebetween. In addition, marginal portions 31b and 33b of the facing sheet 31 and backing sheet 33, which overlap and extend beyond the absorbent batt 35, are also secured together by bead lines 39 of adhesive. If desired, adhesive bead lines may be provided to secure the open network 37 to the absorbent batt 35.

Several different types of facing materials may be used for diaper facing sheet 31. For example, facing sheet 31 may be made up of a mixture of fibers consisting predominately of inexpensive short cellulosic fibers such as wood pulp fibers or cotton linters, in amounts of about 75% to about 98%, the balance being mechanically worked textile fibers of length generally greater than ½ inch, such as rayon as described in U.S. Pat. No. 3,633,348 to Liloia, et al.

Facing sheet materials suitable for use in this invention can have fabric weights in the range of about 1 to 5 oz./yd.$^2$ and densities of less than 0.15 g./cc., generally in the range between 0.05 and 0.1 g./cc. The dry strength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 31 may also be made of an apertured, non-woven fabric which is formed, for example, in accordance with the teachings of commonly assigned U.S. Pat. Nos. 2,862,251, 3,081,514, and 3,081,515. Briefly, such fabrics are foraminous structures wherein groups or groupings of fibers have been rearranged from a fibrous non-woven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known to those skilled in the art. The fabric can be made of naturally occurring fibers, synthetic fibers or blends thereof. Typical facing sheets made of a polyester type material can have a weight of about 0.75 oz./yd.$^2$ In addition, facing sheet 31 can be formed of a non-apertured material, such as a non-woven isotropic web, or the like. In all of the aforementioned facing materials, the material should be relatively hydrophobic so as to retard wicking within the facing layer.

A suitable backing sheet material for the diapers embodying the present invention can be an opaque polyethylene web about 0.001 inch thick. Another suitable material for this purpose is a polyethylene terephthalate web having a thickness of about 0.005 inch.

Figure 6:
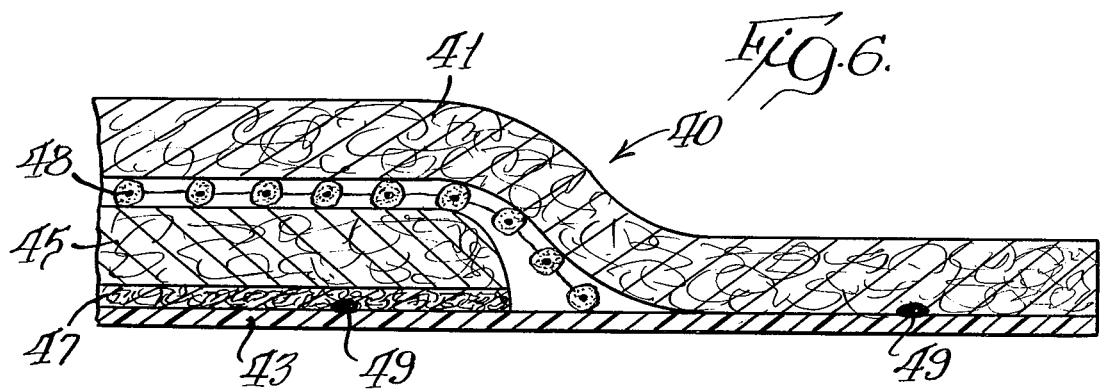
FIG. 6 is a fragmentary cross-sectional elevation similar to FIG. 5, illustrating an alternative embodiment of the invention.

FIG. 6 shows another preferred embodiment which incorporates the absorbent open network of this invention in a diaper having an absorbent pad 45 provided with a highly densified layer 47. The diaper 40 has a moisture permeable facing sheet 41 which is substantially co-extensive with a backing sheet 43. An absorbent batt layer 45 has a densified, highly compacted, lowermost fibrous layer 47 which is adhered to the impervious sheet by bead lines of adhesive 49 substantially throughout the interface therebetween. Marginal portions 41b and 43b also are adhered to each other by bead lines 49. The absorbent open network structure 48 of this invention is situated between the facing sheet 41 and the absorbent batt layer 45. A diaper having an absorbent batt layer as is shown in FIG. 6 is more completely described in U.S. Pat. No. 3,612,005, the disclosure of which is incorporated herein by reference.

In another embodiment of a diaper incorporating the novel absorbent-bearing open network of this invention, the open network may itself comprise the absorbent batt layer. Alternatively, the absorbent-bearing open network may comprise a part of the batt layer, for example, being in the upper third, middle third, or lower third thereof. In another variation, the absorbent batt layer of either of the diapers shown in FIGS. 3 or 4 may have the water-insoluble but water-swellable particles randomly anchored to the fibers that make up the batt.

In yet another embodiment the absorbent-bearing open network may be sandwiched in between two absorbent batt layers. In a further embodiment, the absorbent-bearing open network may be situated between the backing sheet and the absorbent batt layer. All of these embodiments utilizing the absorbent-bearing open network, including both those embodiments shown in FIGS. 4–6 and those discussed without illustration, may be used separately or in combination with each other. As an example, the diaper of FIGS. 4 and 5 could be provided with an absorbent pad means which itself consisted of an absorbent open network structure sandwiched between two absorbent batt layers.

The invention will be illustrated in further detail by the following specific examples. The percentages given are by weight unless otherwise indicated.

The liquid holding capacity given in the following examples is measured by pre-wetting a four-inch diameter sample of a known weight with fifteen times its weight of water, compressing the pre-wetted sample at a pressure of 1.5 pounds per square inch and weighing the compressed sample. The amount of liquid held by a unit weight of the sample after the compression is then calculated and reported as the liquid holding capacity.

The liquid retention for a given sample is the quantity of liquid retained by a unit weight of the sample after spin-drying the pre-wetted sample in a standard laboratory centrifuge.

EXAMPLE I

A two percent solution of a starch polyacrylonitrile hydrocolloid in deionized water is prepared. The solution is padded onto a reticulated polyurethane foam sheet to saturate the sheet. The polyurethane foam sheet has a pore size distribution of 30 to 60 pores per inch, weighs 0.3 ounces per square yard and has an original thickness of 0.15 inch. The saturated foam sheet is passed through a nip formed by a pair of neoprene covered rollers. On passing the foam sheet through the nip, the foam sheet is caused to retain approximately 200 parts of applied hydrocolloid solution per 100 parts of foam. The foam sheet is dried at 240° F. in a through air-drying oven to remove the water. The finished foam structure is found to contain 4 parts of hydrocolloid per 100 parts of foam. The addition of the hydrocolloid increases the ability of the foam sheet to hold water from a liquid holding capacity of 10 cubic centimeters per gram to 14 cubic centimeters per gram and also increases the liquid retention capability of the foam sheet from 0.9 cubic centimeters per gram to 4.1 cubic centimeters per gram.

EXAMPLE II

In this Example, the starting substrate is a 2-ounce lofty non-woven fabric. The fabric has a thickness of about 3.5 inches and is composed of mechanically worked, textile length, 15 denier per filament, crimped polyester fibers. The fibers are bonded with a 15% dry solids add-on of an acrylic binder sold by Rohm & Haas under the designation HA-16. The resulting non-woven fabric is resilient, porous, and wettable. A 5% mixture of a polyacrylonitrile-starch graft copolymer hydrocolloid in deionized water is prepared. The mixture is added onto the 2-ounce lofty polyester non-woven substrate by passing through neoprene nip rolls to provide about 6 ounces of hydrocolloid-deionized water moisture per square yard. The substrate is then passed through a drier operating at 320° F. to flash off the water. The resulting web weighs 2.3 ounces per square yard, is still lofty and contains approximately 0.3 ounces per square yard of the hydrocolloid distributed primarily at bonded polyester fiber intersections. The hydrocolloid material increases the ability of the polyester non-woven substrate to hold water from an original liquid holding capacity of 9 cc./gr. to 10.6 cc./gr. Also, the hydrocolloid improves or increases the liquid retention characteristics of the polyester substrate from 0.3 cc./gr. to 10.28 cc./gr.

EXAMPLE III

A mixture containing four parts of an absorbent, grafted cellulose copolymer hydrocolloid per 100 parts of water is prepared in accordance with U.S. Pat. No. 3,256,372 using deionized water. The mixture is added to an open net fiberglass scrim in an amount sufficient to saturate the scrim. The fiberglass scrim has 8 threads per inch in the machine direction and 8 threads per inch in the cross direction. The saturated scrim is passed under an air knife and dried in a horizontal-through air drier at 300° F. The hydrocolloid material remains on the fiberglass scrim with approximately 9 parts of hydrocolloid per 100 parts of fabric. The hydrocolloid is concentrated primarily at the intersections of the machine and cross direction threads in the scrim. The liquid holding capacity of the untreated fiberglass scrim is about 1 to 1.2 cc./gr. and by adding the hydrocolloid is increased to about 7.3 cc./gr.

EXAMPLE IV

A cotton scrim comprising 21 warp threads of 30/1 cotton count yarn and 11 filling threads of 38/1 cotton count yarn and having a basis weight of 16.2 gr./sq. yard has a liquid holding capacity of about 1.3 cc./gr. An 8% solution of a polyacrylonitrile starch graft copolymer hydrocolloid in deionzied water is added to the scrim, and the scrim is dried. About 1.89 grams of the starch grafted copolymer hydrocolloid per square yard of scrim remains on the scrim. The hydrocolloid is deposited both at the thread crossings as well as on the surface of the component threads. The liquid holding capacity of the scrim is increased to 6.3 cc./gr. by the presence of the hydrocolloid.

The embodiments hereinabove described serve to illustrate the invention but not to limit it. The limits of the invention are defined solely by the claims.

We claim:

1. An absorbent article which consists essentially of an open network structure of fibrous elements defined by a woven scrim having a plurality of intersections, and discrete water-insoluble but water-swellable particles integral with the scrim at the intersections wherein the particles are disposed on and partially envelop the fibrous elements.

* * * * *